United States Patent [19]

Olsen et al.

[11] Patent Number: 5,311,876
[45] Date of Patent: May 17, 1994

[54] AUTOMATIC DETECTION OF SEIZURES USING ELECTROENCEPHALOGRAPHIC SIGNALS

[75] Inventors: Dale E. Olsen, Columbia; Ronald P. Lesser, Baltimore; John C. Harris, Gaithersburg; W. Robert S. Webber, Howard County; John A. Cristion, Columbia, all of Md.

[73] Assignee: The Johns Hopkins University, Baltimore, Md.

[21] Appl. No.: 978,220

[22] Filed: Nov. 18, 1992

[51] Int. Cl.5 .............................................. A61B 5/04
[52] U.S. Cl. .................................................... 128/731
[58] Field of Search ........................................ 128/731

[56] References Cited

U.S. PATENT DOCUMENTS

| | | | |
|---|---|---|---|
| 3,498,287 | 3/1970 | Ertl | 128/731 |
| 3,850,161 | 11/1974 | Liss | 128/731 |
| 4,201,224 | 5/1980 | John | 128/731 |
| 4,214,591 | 7/1980 | Sato et al. | 128/731 |
| 4,545,388 | 10/1985 | John | 128/731 |
| 4,566,464 | 1/1986 | Piccone et al. | 128/731 |
| 4,579,125 | 4/1986 | Strobl et al. | 128/731 |
| 4,873,981 | 10/1989 | Abrams et al. | 128/731 |
| 4,878,498 | 11/1989 | Abrams et al. | 128/731 |
| 5,010,891 | 4/1991 | Chamoun | 128/731 |
| 5,181,520 | 1/1993 | Wertheim et al. | 128/731 |

FOREIGN PATENT DOCUMENTS 1074484 2/1984 U.S.S.R. ............................... 128/731

OTHER PUBLICATIONS

Plumb et al, "I.E.E.E. Transactions on Biomedical Engineering" vol. 11, No. 4, Oct. 1974, pp. 157-159.
Salb, "Medical & Biological Engineering & Computing" vol. 18, No. 3, May 1980, pp. 313-318.
Zschoke, "Electroencephalography & Clinical Neurophysiology", vol. 37, No. 2, Aug. 1974, pp. 191-193.

Primary Examiner—William E. Kamm
Attorney, Agent, or Firm—Francis A. Cooch

[57] ABSTRACT

A patient monitoring system and a method of operating same, including automatically detecting a seizure in the patient, by detecting an electrical discharge in the patient's brain; converting the detected electrical discharge into a digital signal; inputting the digital signal into a microprocessor; detecting a seizure by dividing the digital signals into time segments, preprocessing each time segment including standardizing the signal, reducing the signal in each time segment to a feature, the feature providing information about whether a seizure is occurring using the feature from each time segment; and indicating that a seizure is occurring.

45 Claims, 3 Drawing Sheets

AUTOMATIC DETECTION OF SEIZURES USING ELECTROENCEPHALOGRAPHIC SIGNALS

STATEMENT OF GOVERNMENTAL INTEREST

This invention was made with Government support under contract No. N00039-91-C-5301 awarded by the U.S. Navy Department. The Government has certain rights in this invention.

BACKGROUND OF THE INVENTION

There are an estimated two million people with epilepsy in the United States. Computerized analysis of electroencephalogram (EEG) data has been the goal of many investigators for years. Such an analysis system could be used for diagnosing seizures, for assessing the effectiveness of medical therapy or for selecting patients for epilepsy surgery.

A necessary component of accurate assessment of medical therapy, including safe and effective surgery, requires prolonged EEG monitoring to obtain recordings of seizure activity. One important reason for developing a system is to meet the needs of about one-third of the many patients with complex partial seizures who do not respond satisfactorily to anti-epileptic drug therapy.

Three devices can be developed to assist in the treatment of epilepsy. The first is a microcomputer-based system designed to process massive amounts of electroencephalogram (EEG) data collected during long-term monitoring of patients for the purpose of diagnosing seizures, assessing the effectiveness of medical therapy or selecting patients for epilepsy surgery. Such a device would select and display important EEG events. Currently many such events are missed. A second device would be a portable version of the first. This device would allow the patient to be monitored while away from the hospital. A third device could be implanted and would detect seizures and initiate therapy.

Computerized systems can be used to collect and store the data, but even with new mass-storage devices, it is not practical to store and review all of the data collected over days. Automatic spike and sharp wave detection and automatic seizure detection algorithms could be used to detect critical events and store just the relevant data for later examination by the neurologist and neurosurgeons. This information, in conjunction with clinical observation, is used to localize epileptic form discharges. Reliable automatic seizure detection is perhaps more challenging and would be a key element of any system designed for analysis of EEG data.

Five groups of investigators have pursued the goal of automatic seizure detection by implementing a system and publishing their results. Prior, et. al. (Prior, P. F., Maynard, D. E., "Recording Epileptic Seizures," Proceedings of the Seventh International Symposium of Epilepsy, Berlin (West), Thieme Edition, Publishing Sciences Group, Inc., 325-377 (1975).) developed a simple system aimed at recording the timing and frequency of seizure discharges. They were able to detect severe seizures by looking for large amplitude signals sustained over a period of time. Their system used a single channel of data recorded on paper running at 5 to 6 cm/hour.

Babb, et al. (Babb, T. L., Mariani, E., Crandall, P. H., "An Electronic Circuit for Detection of EEG Seizures Recorded with Implanted Electrodes,"*Electroencephalograph and Clinical Neurophysiology*, 37, 305-308 (1974).) developed electronic circuits for recording and detecting seizures. Their system used implanted electrodes to detect seizures which might otherwise go unreported. The system identified as seizure high-amplitude EEG signals of sufficient duration. They reported monitoring four patients and detecting 66 seizures, 20 of which were false detections. During this same period of time, the nurses detected 28 seizures, two of which were false detections. Therefore, the automated system detected 20 unreported seizures.

Ives, et. al. (Ives, J. R., Thompson, C. J., Gloor, P., "*Seizure Monitoring: A New Tool in Electroencephalography,*" *Electroencephalography and Clinical Neurophysiology*, 41, 422-427 (1976).) used implanted depth electrodes and a PDP-12 computer to remotely monitor patients. The system was adjusted or calibrated for individual patients using their seizure patterns. If the EEG signals fell within an amplitude window for a certain period of time, the algorithm identified the event as a seizure and recorded eight channels of EEG data. During two weeks of monitoring, thirteen seizures were detected and recorded by the computer. Only one seizure was reported by the nursing staff and only 3 were noted by the patient.

If Gotman (Gotman, J., "*Automatic Seizure Detection: Improvements and Evaluations,*" *Electroencephalograph and Clinical Neurophysiology*, 76, 317-324 (1990).) designed a system to select, from largely uneventful EEG data, the sections which are likely to be of interest. Events, such as seizures, are recorded either because the program detects them or because the event button is pressed. His system was originally implemented in 1975 and has been in use since that time. It detects seizures using both surface and depth electrodes. His system is in use in many centers and has been updated. A study of his latest algorithm used 5303 hours of data and showed that 24 percent of the 244 seizures recorded were missed by the automatic detection system. However, in 41 percent of the seizures, the patient alarm was not pressed, but the computer made the decision to record the event. Like the other systems, Gotman's system detects many seizures which would otherwise be missed. The system experiences about one false detection per hour of recording.

Gotman's method uses digitally filtered data broken up into 2-second epochs. He compares features of this data to what he calls "background." The background data is a 16-second long section of data ending 12 seconds prior to the epoch being analyzed. This comparison allows the algorithm to self-scale to account for differences in montage or other settings and is a form of what we will refer to as calibration or standardization. Detection occurs when 1) the average amplitude of half-waves in the epoch is at least three times that of the background, 2) their average duration corresponds to frequencies between 3 and 20 Hz, and 3) the coefficient of variation (ratio of the variance to the square of the mean) of the half-waves is below 0.36. In short, the algorithm is based on amplitude, frequency, and the regularity of the half-wave duration. In 1990, Gotman reported modifications to his algorithm including the requirement to look 8 seconds ahead to verify that the amplitude remains high. This modification reduced false detections.

More recently Murro et al., (Murro, A. M., King. D. W., Smith, J. R., Gallagher, B. B., Flanigin, H. F., Meador, K., "Computerized Seizure Detection of Complex Partial Seizures," *Electroencephalography and Clinical*

*Neurophysiology*, 79, 330–333 (1991).) developed a system using concepts similar to those of Gotman but used spectral concepts for feature development. They used three features from each of two channels. These six features are reduced to four using principal component analysis, and then statistical discrimination is used to develop a detection rule. Their algorithm was developed for intracranial data only.

Murro, et. al. address the issue of calibrating for patient differences partly in the way they define their features. They define reference power as the spectral power between 0.15 and 36 Hz averaged over four consecutive EEG epochs from 27 to 55.6 seconds prior to the event being evaluated. One of their features is relative power and is defined as the power between 0.15 and 36 Hz of the current epoch divided by the reference power. The second of their features is the dominant frequency. The third feature is rhythmicity, which is the ratio of the power associated with the dominant frequency to the relative power. Murro, et. al. use a segment of recent EEG data from the patient to influence the definition of their first and third feature. However, Murro, et al. also provide more in the way of custom tailoring their algorithm to the individual by building a separate decision rule for each patient. Their rule is based on normal data from the patient collected at different times and seizure data collected from other patients. These procedures allow for a more careful calibration for patient differences.

The algorithm of Murro, et. al. was tested using 8 patients and 43 seizures. Their system was evaluated using different detection thresholds. It detected all seizures allowing for a rate of 2.5 false detections per hour and detected 91% of the seizures with 1.5 false detections per hour.

The first seizure detection methods relied on amplitude and duration to identify seizures. Gotman's method tends to mimic the EEG readers. He characterizes the signals using features appearing to be motivated by those observed during seizure activity. His self-scaling and his detection rules are simple but effective.

The methods of Murro, et al. are similar to Gotman's but are more statistically sophisticated. Like Gotman, Murro, et. al., used recent epochs to self-scale their features. They characterize the epochs of data using relative amplitude, dominant frequency and rhythmicity and then use statistical discriminate analysis to develop a detection rule.

There are three important common elements in these two algorithms and in the algorithm of the invention:
1) standardization, calibration or self-scaling
2) feature selection
3) discrimination or a decision rule The most critical element in discriminating seizure from other data is the definition and evaluation of features or feature selection. However, new standardization or calibration methods are also essential.

SUMMARY OF THE INVENTION

The algorithm of the invention has characteristics which make it fundamentally different from those of other investigators. More emphasis is placed on developing and evaluating a variety of features and on developing an improved approach to standardization or calibration called the "self-referencing" system. These two key elements of our algorithm are also applicable to the closely related EEG spike detection problem.

Each channel or time series of EEG data is divided into non-overlapping 3-second epochs of data. The first goal is to compute a probability that the patient is having a seizure for each 3-second segment of data and for each of the different channels processed by the system. These probabilities will be combined with probabilities from adjacent epochs to determine if a patient is having a seizure. To compute the probabilities and reach a conclusion, three steps are necessary. An overview of the basic detection process is diagrammed in FIG. 1.

The first step is the preprocessing step. A 3-second segment or epoch of a signal from a particular channel or location on the head is standardized (calibrated to a standard) using all previously collected epochs from that location. (Standardization is part of the self-referencing system). The intent here is different from that of Gotman's self-scaling in that the current epoch is not simply being evaluated relative to background. The methods are very different and the results are different. However, both provide essential calibration necessary to account for patient differences.

Figure 1A:
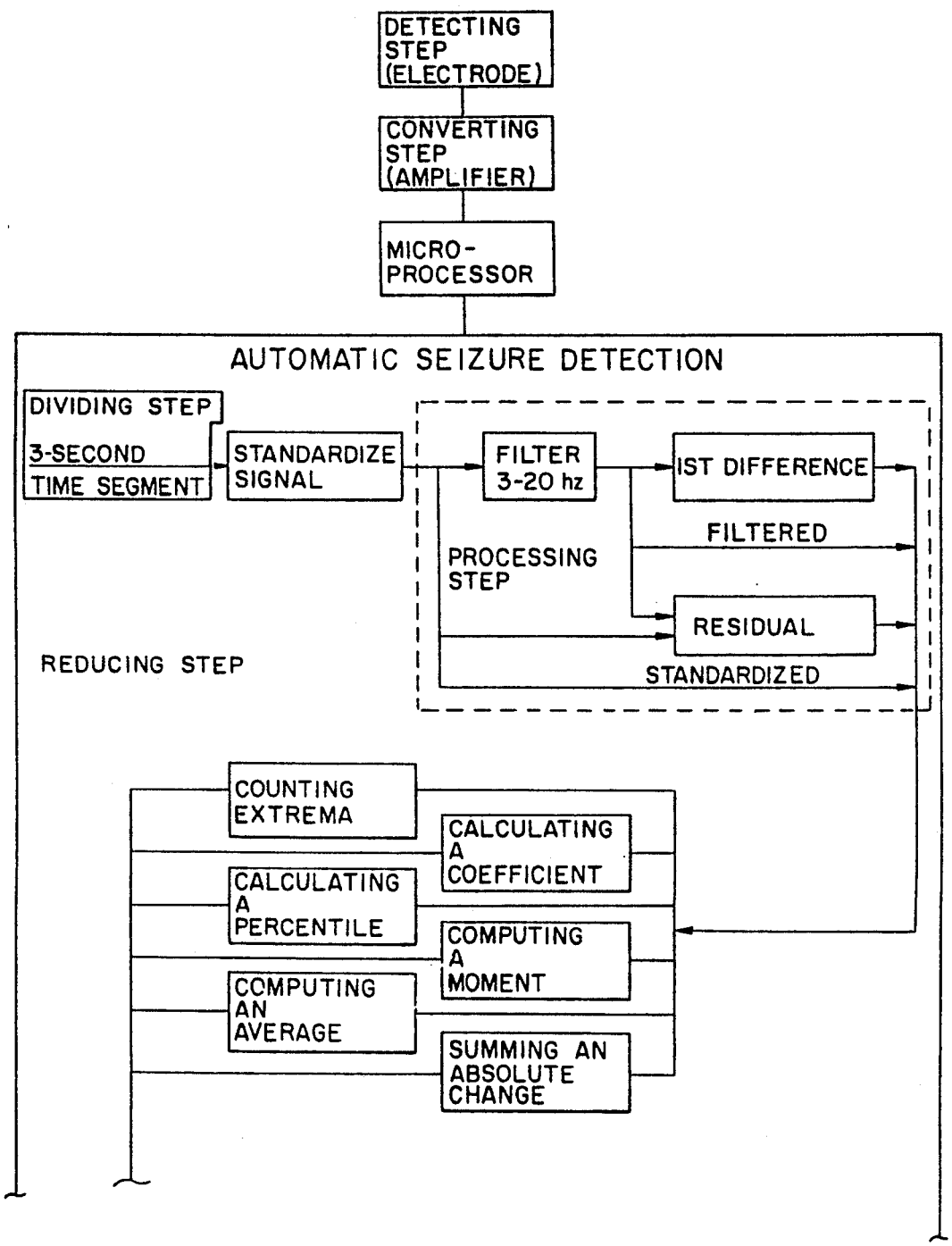
FIG. 1 is a flow diagram of the automatic seizure detection method of the invention.
Figure 1B:
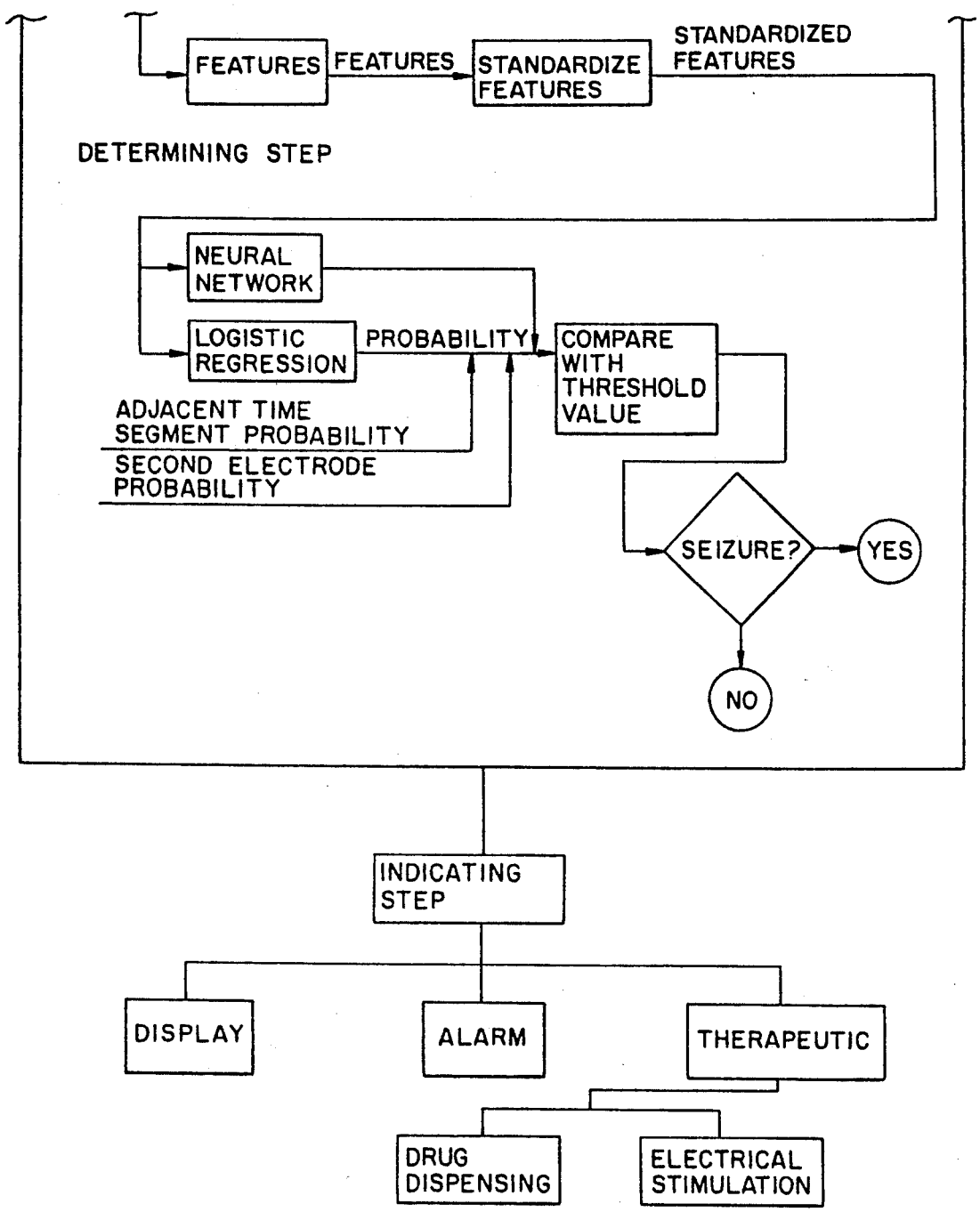

The standardized signal is processed and split into three additional signals (see FIG. 1). Each of the three new signals and the original signal will be used to determine if the patient is having a seizure. The preprocessing step consists of signal standardization and splitting the data. Characteristics or features from each of the four signals are developed in the feature step.

The next step in developing probabilities of seizures is the feature step. In developing this step, data from each epoch is characterized using many features. Each of these features is evaluated to determine which can best help separate seizure and normal data. Once the parameters have been defined, their means and standard deviations are recursively computed for each channel. As a second step in the self reference system, these values are used to standardize the parameters from the incoming epoch of data. Several hundred features have been evaluated. These include usual time-series characteristics, features which mimic EEG readers' methods and statistical characteristics. All three types of features contribute to the discrimination. Algorithms which use all three in combination are better able to detect seizures than those that do not. The feature step consists of computing the most-effective features and standardizing them.

The decision step follows the feature step. Any of the many discriminate techniques could be applied as part of this step. The base algorithm of the invention uses logistic regression. Neural networks and statistical discrimination techniques could easily be applied. A logistic regression model converts the standardized features for the epoch into a probability that a seizure is occurring. Then a decision rule converts the probability together with probabilities from adjacent epochs into a determination of normal or seizure activity.

DETAILED DESCRIPTION OF THE EMBODIMENT

The EEG signal for each epoch is standardized and then it is split to form a standardized, a filtered, a residual, and a first difference signal.

Signal standardization allows amplitude measurements from different locations on the head and different individuals to be scored using a common algorithm. Signal standardization together with feature standardization make up the self-referencing system, a key part of the algorithm of the invention.

The typical method of standardization uses the mean and standard deviation of a signal, calculated for some period of time. The signal is standardized by subtracting off the average value of the signal and dividing the result by the standard deviation of the signal.

The method of the invention uses all past epochs to find the necessary quantities. The standard deviation is calculated recursively (in a running fashion) and updated at each new epoch. This calculation is simplified since the EEG signals have a mean which is essentially zero. Because the raw signal is subject to large amplitude artifacts, the method of the invention calculates the standard deviation from the filtered signal (described below). This provides a more robust value for scaling the data. The recursive calculation is used to update the standard deviation and is given by $$\sigma_+ = \sqrt{\frac{n-1}{n}\sigma_-^2 + \frac{1}{n}\sigma_n^2}$$

where $\sigma_+$, is the standard deviation based on n epochs, $\sigma_-$ is the standard deviation based on the first n-1 epochs, and $\sigma_n$ is the standard deviation based on all of the data in the $n^{th}$ epoch. To keep the raw seizure data in a nominal range, the data from the epoch is divided by $15\sigma_4$. Thus, $$s_n = \frac{r_n}{15\sigma_-}$$

where $r_n$ is the original signal at time n, $s_n$ is the standardized signal and $\sigma_{13}$ is defined above so that the standard deviation, $\sigma$, of the signal is 0.067.

In a real-time system, the standard deviation from the preceding epoch, $\sigma_{13}$, can be used to standardize the current epoch. Since the standardization depends on the filtered signal, this allows the standardization to precede the filtering. The first two epochs should not be standardized and not scored.

The standardized EEG signal is processed so that a total of four signals are formed. The first step in the process is to band-pass filter the signals.

Filtering is a technique for removing unwanted frequencies from a signal. Unwanted signals in the EEG include slow artifacts such as eye-blinks and fast ones due to muscle movement. Our studies show that band-pass filtering to retain the frequencies in the 3-20 hertz range substantially increases the signal-to-noise ratio as reflected in the features. This increase in signal-to-noise was particularly evident in the autoregressive (AR) coefficients.

Although the signal-to-noise ratio is maximized by filtering the signal, there is information of use for discrimination in the other frequencies. The residual frequencies have information which is statistically weaker, but is valuable. The residual signal, $r_i$ is obtained by subtracting the filtered signal, $f_i$ from the standardized one, $s_i$.

$$r_i = s_i - f_i$$

The first difference is a measure of how quickly a signal is changing. It is formed by differencing successive standardized signal points.

$$d_i = S_i - S_{i-1}$$

Note that the differenced epoch will have one fewer points.

Each three-second epoch of processed data consists of 600 measurements of voltage levels. These measurements are reduced to a single value or feature which characterizes the events in that epoch. There are many different ways to reduce the 600 measurements to a single feature. The methods shown in our studies to be particularly useful include calculating 1) the number of extremas, 2) the percentiles, 3) the absolute mean, 4) the autoregressive model parameters, 5) the moments about the mean and 6) the length of the line.

The count of the number of peaks and valleys in the three second epoch is the number of extrema. This feature captures information about both amplitude and frequency. Frequency information is somewhat loosely contained in the count in that high frequency signals will have more extrema. Amplitude information is implicitly in the criteria for deciding how much the signal must change to be considered a peak or a valley. An entire class of features can be constructed, by triggering at a different amplitude change, $\tau$, in defining an extrema. This amplitude change is expressed as a constant factor of the standard deviation used to calibrate the signal. For example, when $\tau$ is 0.067 then the signal must move at least one (filtered) standard deviation (the data is scaled so that the standard deviation is 0.067) before the next high or low point constitutes a peak or valley respectively.

Percentiles are a way of measuring amplitude and duration. They are calculated by ordering the data in the epoch not on a time scale but by the magnitude of the data values. Because the sign of a signal is arbitrary and the signals are somewhat symmetric about zero, the absolute values of the data points are used. The tenth percentile is the data value below which 10% of the absolute value of the signal falls. The median or the $50^{th}$ percentile is the value in the middle of the absolute value of the ordered data. As the amplitude of the signal increases, the percentile also increases. Since the intent is to develop an algorithm which works at different locations on the head, the absolute value of the signal is used to eliminate directionality associated with a particular location.

The absolute mean is the average of the absolute value of the data. This feature measures amplitude information and lacks much of the duration information implicit in the percentiles.

The autoregressive (AR) features are the coefficients used to predict where the signal is going, given the preceding several points. The model used assumes that the mean of the $n^{th}$ point is given by $$y_n = a_1 y_{n-1} + a_2 y_{n-2} + \ldots + a_{10} y_{n-10}$$

where $y_n$ is the voltage measured at time n. Each 3-second epoch of the filtered (3–20 Hz) signal was modeled with ten parameter AR model. (The sampling rate is 200 Hz). The coefficients are calculated from a least-squares fit through each ten-point segment in the epoch. Thus, the AR coefficients, $a_i$ are the solution to the normal equations:

$$a = (A^T A)^{-} A^T b$$

where $$A = \begin{bmatrix} y_{10} & y_9 & y_8 & \cdots & y_1 \\ y_{11} & y_{10} & y_9 & \cdots & y_2 \\ y_{12} & y_{11} & y_{10} & \cdots & y_3 \\ \cdot & \cdot & \cdot & & \cdot \\ \cdot & \cdot & \cdot & & \cdot \\ \cdot & \cdot & \cdot & & \cdot \\ y_{599} & y_{598} & y_{593} & \cdots & y_{590} \end{bmatrix},$$

$$a = [a_1, a_2, \ldots, a_{10}]^t$$

and $$b = [y_{11}, y_{12}, y_{13}, \ldots, y_{600}]^t$$

The shape of the distribution of the 600 measurements in an epoch can be described using moments. The most common example is the mean. The square-root of the second moment about the mean is standard deviation. These two moments identify the center and the dispersion of the data.

The higher order moments, such as skewness (third) and kurtosis (fourth) are useful for describing asymmetric or flat distributions and can be used as features. Even higher order moments (fifth and sixth) can be useful in closely approximating the shape of a distribution. For our purposes, higher-order moments are expressed relative to the standard deviation and have been shown to be useful in separating seizure and normal data. We calculate the higher-order moments for the epoch sample. These calculations are straight-forward extensions of the commonly used skewness and kurtosis. The odd moments (third, fifth) are expressed in absolute value about the epoch mean.

The line length is the sum of the absolute change in the signal amplitudes during the epoch.

Feature standardization allows features from different head locations and different individuals to be scored using a common algorithm. It is an important part of the self referencing system of the invention. It does for all features what signal standardization does for amplitude. In fact, signal standardization is required only so that the class of extrema parameters can be calculated. A feature, $f_n$, is standardized at epoch n by the recursive estimate of the mean, $\bar{f}_n$, and the standard deviation, $S_{ns}$, of that feature. The standard formulas for the mean and variance of n features can be written as $$\bar{f}_n = \frac{1}{n} \sum_1^n f_i \text{ and } S_n^2 = [T_n - (\bar{f}_n)^2]$$

where $$T_n = \frac{1}{n} \sum_1^n f_i^2.$$

For a real-time system, the mean and variance must be updated each time a new feature is computed or every three seconds. The formulas below are used to update these values.

$$\bar{f}_n = \left( \frac{n-1}{n} \right) \bar{f}_{n-1} + \left( \frac{1}{n} \right) f_n$$

and $$S_n^2 = T_n - (\bar{f}_n)^2 \text{ where } T_n = \left( \frac{n-1}{n} \right) T_{n-1} + \left( \frac{1}{n} \right)(f_n)^2.$$

To start the recursive formulas, use $\bar{f}_1 = f_1$ and $T_1 = f_1^2$. Since it is not possible to compute a variance with only one epoch, standardization is not performed during the first two epochs.

The decision step consists of the application of logistic regression and a decision rule. From the feature described above and other classes of features, several hundred features have been computed and evaluated. The logistic regression equation rule is used to convert the most useful features into a probability that the patient is having a seizure. This probability or decision value can then be used as a basis for deciding if a patient is having a seizure.

Any of several discrimination techniques could be used to convert the features from an epoch into a decision value including a neural net, statistical discriminant analysis, or logistic regression. Logistic regression is used because it 1) produces a decision value which is valid probability of seizure, 2) allows the joint evaluation of many features and 3) has been successfully used for many other applications. A decision rule (discussed below) allows the decision values from this and other epochs, either at different head locations or successive times, to be combined into a final determination.

A logistic regression model (LOGIT) is used to combine an epoch's features into a probability that a seizure is occurring using a single epoch. The logit model has the form:

$$P(\text{seizure}) = \frac{e^{\text{score}}}{1 + e^{\text{score}}}$$

where:

score = $\omega_0 + \omega_1 \cdot \text{feature}_1 + \omega_2 \cdot \text{feature}_2 + \omega_3 \cdot \text{feature}_3 + \ldots + \omega_9 \cdot \text{feature}_9$ The exact weighting and features used in the logit model depend entirely on the data used to develop the model. As the database increases, the exact features and weights used are likely to change. However, they will be drawn from the classes of features described above. We have found that the combination of features and weights shown in Table I below predicted seizures well.

TABLE 1

| FEATURE (Standardized) | WEIGHTS |
|---|---|
| Raw #Extrema $\tau$ = .30 | 1.7340 |
| Filtered \|40th\| Percentile | 1.7359 |
| Filtered #Extrema $\tau$ = .35 | 0.7855 |

TABLE 1-continued

| FEATURE (Standardized) | WEIGHTS |
|---|---|
| Residual Extrema $\tau = .30$ | −2.4593 |
| Residual #Extrema $\tau = .001$ | 4.7388 |
| 1st Difference $|\mu|$ | −0.7192 |
| 1st Difference #Extrema $\tau = .065$ | 2.2524 |
| Filtered $a_1$ | −12.5495 |
| Filtered $a_2$ | −13.9512 |
| $\omega_0$ | −19.0326 |

Figure 2:
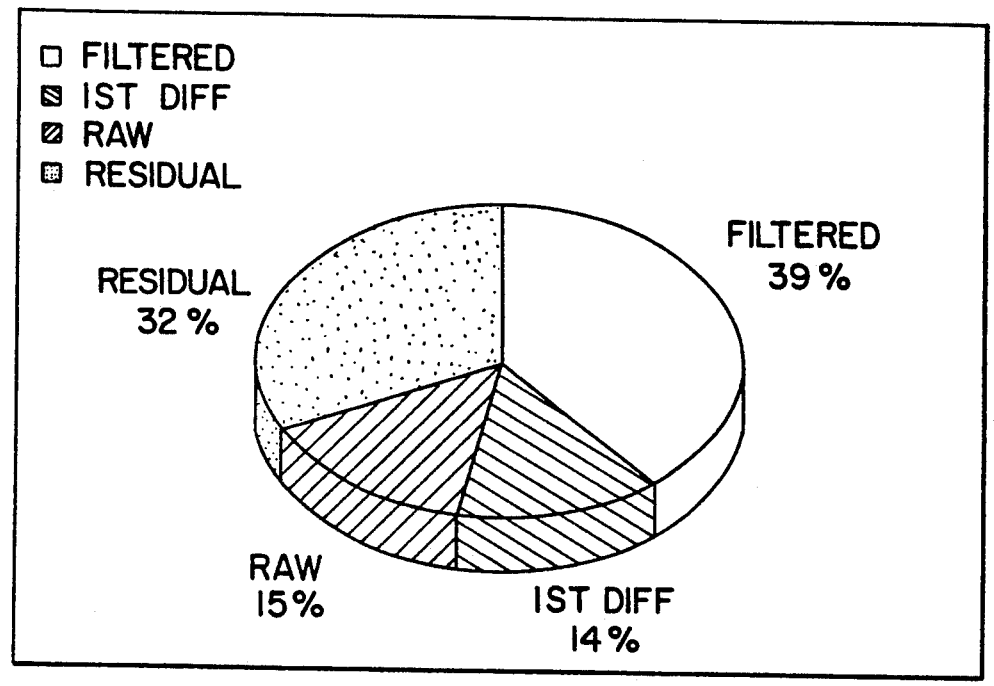
FIG. 2 illustrates in pie chart form the weights given to the contributions of different signals.
Figure 3:
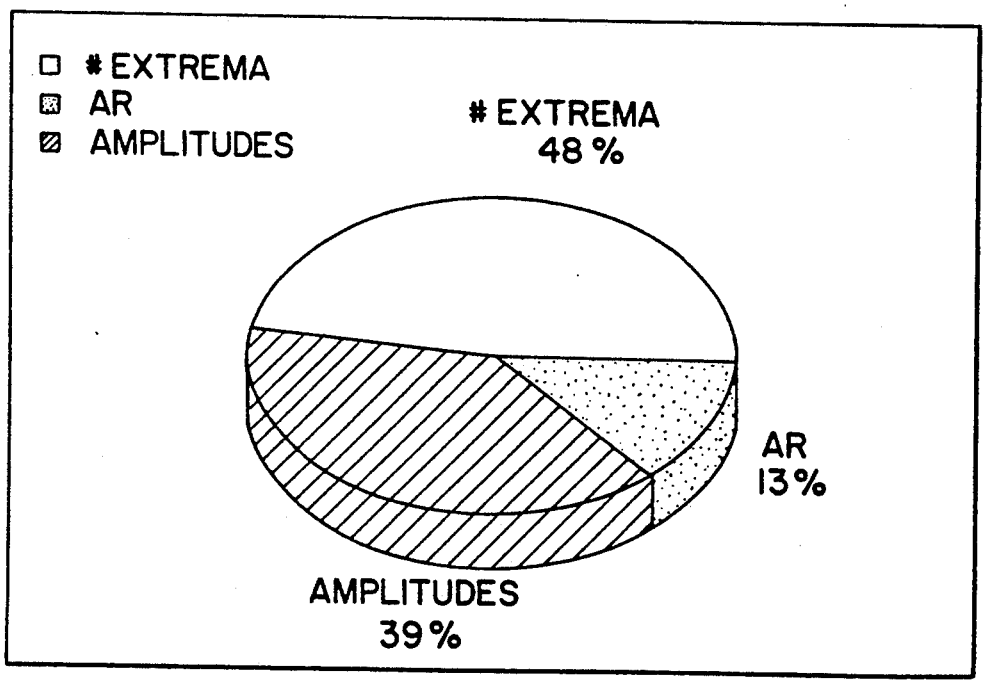
FIG. 3 illustrates in pie chart form the weights given by the method of the invention to different classes of features.

The model fit of our data resulted in the weight, as shown in FIG. 2, being given to each of the signals. FIG. 3 shows the weights given by the algorithm to the different classes of features.

For each epoch and each channel being monitored, a probability of seizure is computed. A determination of seizure can be made in two ways:

1) the probability from any epoch exceeds a certain threshold, say, 0.99990.
2) the probability from any channel exceeds a certain threshold, say, 0.80 for two successive epochs and also exceeds this threshold at least one other channel during either of those two epochs.

These thresholds can be adjusted as necessary to minimize false alarms or to maximize detection. The second criterion has proven most effective.

The critical measure of an algorithm's performance is not how well it detects seizures, but how well it detects seizures without producing false detections. It is a simple matter to demonstrate that an algorithm correctly identifies seizures on a limited span of data. The algorithm of the invention has been applied to several spans of seizure data from six different patients and all seizures were detected with no false detections. The difficulty comes when extending an algorithm's use to days of data.

Five-minute segments of data were collected from each of two patients, both day and night, over a five-day period. The segments were sampled at least once per hour with an effort being made to record a variety of activity and sleep stages. Nine seizures (some lasting over 10 minutes) were recorded, five from one patient and four from the other. Seven and one-half hours of sampled data were saved. An initial algorithm was developed for two channels from one patient and was successfully applied to the second. All seizures in both patients were detected and there were no false detections.

The algorithm of the invention was developed using all 35,000 epochs of standardized data from both patients. Seizure onset for one patient was on the left temporal region and for the second was on the right. As a result, data from FP1–F7, F7–T3, T3–T5, and T5–01 from the first patient and data from FP2–F8, F8–T4, T4–T6, and T6–02 from the second were used as example data to build the algorithm. When the algorithm was applied to the sampled data, all seizures were detected and there were no false detections.

The algorithm of the invention used logistic regression to identify the most useful features and to form a decision rule. Unlike neural networks, logistic regression selects only about 5–15 constants and therefore cannot over-train or memorize even with much smaller data sets. As a result, the testing on 35,000 epochs of data described above provides significant evidence of the discrimination capability of the algorithm.

As noted in the Background, the seizure detection algorithm of the invention will be to monitor patients in long-term epilepsy monitoring units. Most of these data will be from surface electrodes. A personal computer-based system could be designed, built and marketed for use in hospitals equipped to treat epilepsy. The system would save spikes, sharp waves and seizure data for later analysis by neurologists and neurosurgeons and for medical records. Then a portable version of the system could be built, perhaps even using commercially available computers. The compact system would be able to continuously monitor the patient at home for a day before the data would be down-loaded to a larger computer. The system could significantly reduce hospitalization time and costs and be of substantial benefit to the patient.

Another use of an automatic seizure detection system derives from the research in the use of electrical stimulation to control epileptic seizures. Researchers have stimulated the vagus nerve, and electrically stimulated the centromediam thalamic nucleus. Both means significantly reduced clinical seizures. An implanted device to control or prevent epileptic seizures has been produced, tested and patented. This device proved most effective for the patients who can feel a seizure coming on and then use a small magnet to initiate the stimulation of the vagus nerve. These reports, coupled with the possibility of drug therapy initiated using an implanted device, suggest that an implanted automatic seizure detection device, coupled with a therapeutic device, could be developed and used to significantly reduce the frequency, intensity or duration of seizures.

A miniaturized monitoring system could be built and implanted in the patient. Since the data for this application would be from implanted electrodes, the seizure detection algorithm would not need to deal with muscle and other artifacts or the effects of the skull on the electrical signals. The algorithm could be adapted to the patient. Based on experience with more difficult surface detection algorithms, we believe that a highly reliable detection algorithm can be developed. In still other respects this device is simpler. Only a few channels would need be monitored. The storage of large data sets and spike and sharp wave detection would not be needed.

The development of new medical procedures has enabled neurologists and neurosurgeons to provide safe and effective treatment of otherwise intractable epilepsy. At the same time, the development of computer technology has made it possible to collect and process more information than ever before. A key element to improving the general care of patients with intractable epilepsy will be the algorithm of the invention which will enable the computers to efficiently reduce the data collected to information useful in planning therapy or to initiate treatment in a timely fashion.

We claim:

1. A method of operating a patient monitoring system wherein a seizure in the patient is automatically detected comprising the steps of:
   detecting an electrical discharge in the patient's brain;
   converting the detected electrical discharge into a digital signal;
   inputting the digital signal into a microprocessor;
   detecting automatically a seizure using the microprocessor and the digital signal comprising the steps of:
   dividing the digital signal into a plurality of time segments;

standardizing the digital signal in each time segment;

processing the standardized digital signal in each time segment to form at least one additional signal in each time segment;

reducing each signal in each time segment to a feature, the feature providing information about whether a seizure is occurring;

standardizing each feature; and determining whether a seizure is occurring using the standardized features from each time segment; and indicating that a seizure is occurring.

2. The method as recited in claim 1, wherein each time segment is three seconds in length.

3. The method of operating a patient monitoring system as recited in claim 1, the electrical discharge detecting step comprising the step of attaching a plurality of electrodes to the patient.

4. The method as recited in claim 3, wherein the determining step comprises the step of converting the standardized features from each time segment into a probability that a seizure is occurring.

5. The method as recited in claim 4, wherein the standardized features converting step comprises the step of using logistic regression to convert the standardized features into a probability that a seizure is occurring.

6. The method as recited in claim 5, wherein the determining step further comprises the step of converting the probabilities for adjacent time segments into a determination that a seizure is occurring.

7. The method as recited in claim 6, wherein the determining step further comprises the step of deciding whether the probabilities for adjacent time segments from an electrode exceed a threshold value and a probability for a time segment from a second electrode also exceeds the threshold value during either of the two adjacent time segments.

8. The method of operating a patient monitoring system as recited in claim 4, the determining step further comprising the step of comparing the probability that a seizure is occurring to a threshold value.

9. The method as recited in claim 1, the processing step comprising the step of filtering the digital signal.

10. The method as recited in claim 9, wherein the processing step further comprises:

subtracting the filtered digital signal from the standardized digital signal to obtain a residual digital signal; and differencing successive standardized digital signal points to obtain a first difference digital signal.

11. The method as recited in claim 1, wherein the reducing step comprises the step of counting in a signal of the time segment, the signal containing a plurality of extrema, the number of the extrema in the signal.

12. The method as recited in claim 1, wherein the reducing step comprises the step of calculating a percentile of an absolute value of a signal in the time segment.

13. The method as recited in claim 1, wherein the reducing step comprises the step of computing an average of the absolute value of a signal in the time segment.

14. The method as recited in claim 1, wherein the reducing step comprises the step of calculating a coefficient for an autoregressive time series model of a signal in the time segment.

15. The method as recited in claim 1, wherein the reducing step comprises the step of computing a moment for a signal in the time segment.

16. The method as recited in claim 1, wherein the reducing step comprises the step of summing an absolute change in an amplitude of a signal in the time segment.

17. The method of operating a patient monitoring system as recited in claim 1, the detected electrical discharge converting step further comprising the step of amplifying the digital signal.

18. The method of operating a patient monitoring system as recited in claim 1, wherein the determining step comprises the step of using a neural network to convert the standardized features into a determination that a seizure is occurring.

19. The method of operating a patient monitoring system as recited in claim 1, the indicating step comprising the step of displaying the signals from each time segment.

20. The method of operating a patient monitoring system as recited in claim 1, the indicating step comprising the step of sounding an alarm when a seizure is determined to be occurring.

21. The method of operating a patient monitoring system as recited in claim 1, further comprising the step of providing treatment to the patient when a seizure is determined to be occurring.

22. The method of operating a patient monitoring system as recited in claim 21, the treatment providing step comprising the step of electrically stimulating the patient to control the seizure.

23. The method of operating a patient monitoring system as recited in claim 21, the treatment providing step comprising the step of dispensing a drug to the patient to control the seizure.

24. A patient monitoring system for automatically detecting a seizure, the monitoring system comprising:

means for detecting an electrical discharge in the patient's brain;

means for converting the detected electrical discharge into a digital signal;

a microprocessor for receiving the digital signal;

means for automatically detecting a seizure using the microprocessor and the digital signal, the automatic detection means comprising:

means for dividing the digital signal into a plurality of time segments;

means for standardizing the digital signal in each time segment;

means for processing the standardized digital signal in each time segment to form at least one additional signal in each time segment;

means for reducing each signal in each time segment to a feature, the feature providing information about whether a seizure is occurring;

means for standardizing each feature; and means for determining whether a seizure is occurring using the standardized features from each time segment; and means for indicating that a seizure is occurring, the indicating means being connected to the automatic detection means.

25. The patient monitoring system as recited in claim 24, the electrical discharge detecting means comprising a plurality of electrodes.

26. The patient monitoring system as recited in claim 25, the means for determining whether a seizure is occurring comprising a means for converting the standardized features from each time segment into a probability that a seizure is occurring.

27. The patient monitoring system as recited in claim 26, the means for determining whether a seizure is occurring further comprising a means for comparing the probability that a seizure is occurring to a threshold value.

28. The patient monitoring system as recited in claim 26, the feature converting means comprising means for using logistic regression to convert the standardized features into a probability that a seizure is occurring.

29. The patient monitoring system as recited in claim 28, the means for determining whether a seizure is occurring further comprising a means for converting the probabilities for adjacent time segments into a determination that a seizure is occurring.

30. The patient monitoring system as recited in claim 29, the means for determining whether a seizure is occurring further comprising a means for deciding whether the probabilities for adjacent time segments from an electrode exceed a threshold value and a probability for a time segment from a second electrode also exceeds the threshold value during either of the two adjacent time segments.

31. The patient monitoring system as recited in claim 24, the detected electrical discharge converting means further comprising an amplifier for amplifying the digital signal.

32. The patient monitoring system as recited in claim 24, the digital signal processing means comprising a filter.

33. The patient monitoring system as recited in claim 32, the digital signal processing means further comprising:
    means for subtracting the filtered digital signal from the standardized digital signal to obtain a residual digital signal; and
    means for differencing successive standardized digital signal points to obtain a first difference digital signal.

34. The patient monitoring system as recited in claim 24, the determining means comprising a neural network means to convert the standardized features into a determination that a seizure is occurring.

35. The patient monitoring system as recited in claim 24, the reducing means comprising a means for counting in a signal of the time segment, the signal containing a plurality of extrema, the number of the extrema in the signal.

36. The patient monitoring system as recited in claim 24, the reducing means comprising a means for calculating a percentile of an absolute value of a signal in the time segment.

37. The patient monitoring system as recited in claim 24, the reducing means comprising a means for computing an average of the absolute value of a signal in the time segment.

38. The patient monitoring system as recited in claim 24, the reducing means comprising a means for calculating a coefficient for an autoregressive time series model of a signal in the time segment.

39. The patient monitoring system as recited in claim 24, the reducing means comprising a means for computing a moment for a signal in the time segment.

40. The patient monitoring system as recited in claim 24, the reducing means comprising a means for summing an absolute change in an amplitude of a signal in the time segment.

41. The patient monitoring system as recited in claim 24, the indicating means comprising means for displaying the signals from each time segment.

42. The patient monitoring system as recited in claim 24, the indicating means comprising alarm means.

43. The patient monitoring system as recited in claim 24, further comprising a therapeutic means connected to the automatic detection means for providing treatment to the patient.

44. The patient monitoring system as recited in claim 43, the therapeutic means comprising a means for electrically stimulating the patient to control the seizure.

45. The patient monitoring system as recited in claim 43, the therapeutic means comprising a means for dispensing a drug to the patient to control the seizure.

* * * * *